United States Patent
Simon et al.

(12)

(10) Patent No.: US 6,358,728 B1
(45) Date of Patent: Mar. 19, 2002

(54) MUTATIONS IN NUCLEIC ACID MOLECULES ENCODING 11-CIS RETINOL DEHYDROGENASE, THE MUTATED PROTEINS, AND USES THEREOF

(75) Inventors: András Simon; Ulf Eriksson, both of Stockholm (SE); Thaddeaus P. Dryja, Boston, MA (US); Eliot L. Berson, Boston, MA (US); Hioyuji Yamamoto, Boston, MA (US)

(73) Assignees: The President & Fellows of Havard College, Cambridge; Massachusettes Eye & Ear Infirmary, Boston, both of MA (US); Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/880,427

(22) Filed: Jun. 13, 2001

Related U.S. Application Data

(62) Division of application No. 09/306,538, filed on May 6, 1999.

(51) Int. Cl.[7] .......................... C12N 1/20; C12N 15/00; C12N 9/04; C07H 21/04
(52) U.S. Cl. .............................. 435/252.3; 435/252.33; 435/320.1; 435/190; 435/325; 536/23.2
(58) Field of Search .......................... 435/252.3, 252.33, 435/320.1, 190, 325; 536/23.2

(56) References Cited

FOREIGN PATENT DOCUMENTS

WO      WO 97/19167      5/1997

OTHER PUBLICATIONS

Simon et al. [Genomics 36 : 424–430 (1996)].*
Cideciyan, et al., "Rod Plateaux During Dark Adaptation In Fundus Albipunctatus Caused By a Null Mutation in The 11–CIS–Retinol Dehydrogenase Gene," IOVS 41(4):S532 (Not Prior Art) (Mar. 15, 2000).
Gonzalez–Fernandez, et al., "11–cis Retinol dehydrogenase mutations as a major cause of the congenital night–blindness disorder known as fundus albipunctatus," Mol. Vis 5(41):1–6 (Dec. 30, 1999) (Not Prior Art).
Harris, et al., "Screen For Mutations In The Gene Encoding 11–CIS Retinol Dehydrogenase In Patients With Retinitis Pigmentosa Or An Allied Disease," Invest. Ophthal. & Vis. Sci. 37(3):S383 (Feb. 15, 1996).
Hirose, et al., "Mutations In The 11–CIS Retinol Dehydrogenase Gene In A Form Of Fundus Albipunctatus In Japan," IOVS 41(4): S615 (Mar. 15, 2000) (Not Prior Art).
Kurz, et al., "Mutations In 11–CIS Retinol Dehydrogenase Membrane Anchor Region Cause A Form Of Fundus Albipunctatus With Fading Spots," IOVS 41(4): S615 (Mar. 15, 2000) (Not Prior Art).
Simon, et al., "The Retinol Pigment Epithelial–specific 11–cis Retinol Dehydrogenase Belongs to the Family of Shrot Chain Alcohol Dehydrogenases," J. Brol. Chem 270(3):1107–1112 (Jan. 20, 1995).
Wada, et al., "Clinical Variability of Patients Associated With Gene Mutations Of Visual Cycle Protein: Arrestin, RPE65 and RDH5 Genes," 41(4):S617 (Mar. 15, 2000) (Not Prior Art).
Yamamoto, et al., "Three Novel Mutations In the RDH5 Gene Encoding 11–cis Retinol Dehydrogenase In Patients With Fundus Albipunctatus," IOVS 41(4):S615 (Mar. 15, 2000) (Not Prior Art).
Yamamoto, et al., "Mutations In The Gene Encoding 11–cis Retinol Dehydrogenase (RDH1) In Patients With Fundus Albipunctatus," IOVS 40(4):S601 (Mar. 15, 1999).
Young, et al., "11–cis Retinol Dehydrogenase (RDH5) Gene Mutations In Fundus Albipunctatus Patients," IOVS 41(4):S615 (Mar. 15, 2000) (Not Prior Art).

* cited by examiner

*Primary Examiner*—Ponnathapu Achuta Murthy
*Assistant Examiner*—Tekchand Saidha
(74) *Attorney, Agent, or Firm*—Fulbright & Jaworski,

(57) ABSTRACT

The invention relates to mutations in the gene encoding 11-cis retinal dehyrogenase. The mutations in the gene and in the resulting encoded protein are correlated to ocular disorders, such as fundus albipunctatus.

7 Claims, 2 Drawing Sheets

MUTATIONS IN NUCLEIC ACID MOLECULES ENCODING 11-CIS RETINOL DEHYDROGENASE, THE MUTATED PROTEINS, AND USES THEREOF

RELATED APPLICATION

This application is a divisional of Ser. No.: 09/306,538, filed May 6, 1999.

FIELD OF THE INVENTION

This invention relates to mutations in nucleic acid molecules encoding the protein 11-cis retinol dehydrogenase, or "RDH5," and the resulting mutated protein. These mutations are implicated in ocular disorders, such as fundus albipunctatus. The diagnostic and therapeutic ramifications of these mutations are also discussed and are features of the invention.

BACKGROUND AND PRIOR ART

Retinoids (vitamin A-derivatives) have important physiological functions in a variety of biological processes. During embryonic growth and development, as well as during growth and differentiation of adult organisms, retinoids act as hormones and participate in the regulation of gene expression in a number of cell types. See Lied et al. Trends Genet., 17:427–433 (1992). It is believed that these effects are medicated through two classes of nuclear ligand-controlled transcription factors, the retinoic acid receptors (RARs) and the retinoid X receptors (RXRs), Benbrook et al., Nature, 333:669–672 (1988); Brand et al., Nature, 332:850–853 (1988); Giguere et al., Nature, 330:624–629 (1987); Mangelsdorf et al., Nature, 345:224–229 (1990); Mangelsdorf, et al. Genes Dev. 6:329–344 (1992); Petkovich et al. Nature 330:440–450 (1987); and Zelent et al., Nature 339:714–717 (1989).

Apart from their function as hormones in cellular growth and differentiation, retinoids are also involved in the visual process, as the stereo isomer 11-cis retinaldehyde is the chromophore of the visual pigments. See, e.g. Bridges, *The Retinoids*, Vol. 2, pp 125–176, Academic Press, Orlando, Fla., (1984).

Under normal physiological conditions most cells, both ocular and non-ocular, obtain all-trans retinol as their major source of retinoids. Despite the many different metabolic events taking place in different tissues, it is known that a common extracellular transport machinery for retinol has evolved. Specifically, in plasma, retinol is transported by plasma retinol binding protein (RBP). See Goodman et al., *The Retinoids*, Academic Press, Orlando Fla., Volume 2, pp. 41–88 (1984). The active derivatives of retinol, retinoic acid in non-ocular tissues and mostly 11-cis retinaldehyde for ocular tissues, are then generated by cellular conversion using specific mechanisms. To date, none of these mechanisms have been fully defined at the molecular level and several of the enzymes involved have only been identified by enzymatic activities. See Lion et al., Biochem. Biophys. Acta. 384:283–292 (1975); Zimmermann et al., Exp. Eye Res. 21:325–332 (1975); Zimmerman, Exp. Eye Res. 23:159–164 (1976) and Posch et al., Biochemistry 30:6224–6230 (1991).

Polarized retinal pigment epithelial cells (RPE) are unique with regard to retinoid uptake since all-trans retinol enters these cells via two different mechanisms. Retinol accumulated from RBP is taken up through the basolateral plasma membrane, while all-trans retinol, presumably taken up from the interstitial retinol-binding protein (IRBP) following bleaching of the visual pigments, may enter through the apical plasma membrane. See Bok et al., Exp. Eye Res. 22:395–402 (1976); Alderetal., Biochem. Biophys. Res. Commun. 108:1601–1608(1982); Lai et al., Nature 298:848–849 (1982); and Inu et al., Vision Res. 22:1457–1468 (1982).

The transfer of retinol from RBP to cells is a subject under investigation. In a number of cell types, including RPE, specific membrane receptors for RBP have been identified, which is consistent with a receptor-mediated uptake mechanism for retinol. For example, isolated retinol binding protein receptors, nucleic acid molecule coding for these receptors and antibodies binding to the receptor are known. . These teachings relate to the first of the two mechanisms. See Bavik et al., J. Biol. Chem. 266:14978–14985 (1991); Bavik, et al. J. Biol. Chem. 267:23035–23042 1992; Bavik et al., J. Biol. Chem. 267:20540–20546 (1993); and U.S. Pat. Nos. 5,573,939 and 5,679,772, all of which are incorporated by reference. See also Heller, J. Biol. Chem. 250:3613–3619 (1975); and Bok et al., Exp. Eye Res. 22:395–402 (1976).

Retinol uptake on the apical side of the RPE for the regeneration of 11-cis retinaldehyde ("11-cis retinal" hereafter) is less well characterized. However, regardless of the origin of all-trans retinol, the synthesis and apical secretion of 11-cis retinal seems to be the major pathway for accumulated retinol in the RPE. At present, it is not known whether similar mechanisms are used with regard to cellular retinol uptake through the basolateral and the apical plasma membranes. However, available data show that functional receptors for RBP are exclusively expressed on the basolateral plasma membrane of RPE-cells. Bok et al., Exp. Eye Res. 22:395–402 (1976).

It is also known that retinal pigment epithelial cells (RPE) express a 63 kDa protein (p63). It has also been shown by chemical cross-linking that this protein may be part of an oligomeric protein complex which functions as a membrane receptor for plasma retinol-binding protein (RBP) in RPE-cells, or a component of the retinoid uptake machinery in RPE cells. See Bavik et al., J. Biol. Chem. 266:14978–14875 (1991); Bavik et al., J. Biol, Chem. 267:23035–23042 (1992), and U.S. Pat. Nos. 5,573,939 and 5,679,772 The p63 protein has been isolated and the corresponding cDNA cloned. See Bavik et al., J. Biol. Chem. 267:20540–20546 (1993)and the '939 and '772 patents referred to supra. All of these references are incorporated by reference.

11-cis retinal, referred to supra is important in vision, because it is the light sensing chromophore found in cone opsins and rod opsins (i.e., "rhodopsin"), in both cone and rod photoreceptor cells. Deficiencies in vitamin A result in reduction in concentrations of rhodopsin in the retina, which is followed by night blindness. In turn, if night blindness is left untreated it is followed by degeneration of rod photoreceptors, and then cone photoreceptors. In fact, vitamin A supplementation has been reported to slow the course of retinal degeneration in diseases such as retinitis pigmentosa (Berson et al, Arch. Ophthalmol111:761–772(1993), and to reverse the night blindness found least temporarily. See Jaconson, et al, Nature Genet. 11:27–32(1995).

Deficiencies in vitamin A can be attributed to one or more causes, including poor diet, or a deficiency in one or more of the proteins involved in transport of vitamin A through the bloodstream. See, e.g., Wetterau, et al., Science 258:999–1001 (1992), and Narcisi, et al., Am. J. Hum. Genet 57:1298–1310 (1995), discussing an inherited deficiency in microsomal triglyceride transfer protein, and Seeliger, et al., Invest. Ophthal Vis. Sci. 40:3–11 (1999), discussing an inherited deficiency in serum retinol binding protein.

Physiological abnormalities and visual symptoms also arise from defects in the storage or metabolism of vitamin A within the retina. With respect to the storage of the vitamin, a number of proteins are thought to bind 11-cis and all-trans vitamin A alcohols and aldehydes in the retina and the retinal pigment epithelium. These proteins include "CRALBP", or cellular relinaldehyde binding protein, "IRBP", or "interphotoreceptor retinoid binding protein", and "CRBP", or cellular retinol-binding protein. CRALBP and IRBP are known to be essential to photoreceptor physiology, since null mutations in the genes encoding these proteins cause photoreceptor degeneration in mammals. See Mau, et al., Nature Genet 17:198–200 (1997); Morimura, et al., Invest. Ophthalmal. Vis. Sci. 40:1000–1004 (1999); Burstedt, et al., Invest. Ophthal. Vis. Sci. 40:995–1000 (1999); Liou, et al., J. Neurasci 18:4511–4520 (1998).

In contrast to the understanding of the pathways and mechanisms discussed supra, abnormalities in the metabolic pathways which convert all-trans retinol from the bloodstream into 11-cis retinal, and that reconvert the all-trans retinal produced after cone and rod photopigments absorb photons of light back to 11-cis retinol are not well understood. Various enzymes are involved in this pathway, and are found in photoreceptor cells, as well as neighboring retinal pigment epithelium, and Muller cells of the retina. Several of these enzymes have been purified only recently. For example, see Simon et al., J. Biol. Chem 270:1107–1112 (1995), and U.S. Pat. No. 5,731,195, both of which are incorporated by reference for teachings relating to purified 11-cis retinal dehydrogenase, and molecules encoding this enzyme, Haeseleer, et al., J. Biol. Chem 273:21790–21799 (1998), for teachings related to all-trans retinal oxido reductase, and Ruiz, et al., J. Biol. Chem 274:3834–3841 (1999), for teachings relating to It has now been found that ocular disorders are associated with mutations in the nucleic acid molecules encoding 11-cis retinal dehydrogenase (RDH5), and the resulting mutated proteins. These are features of the invention which are set out in the disclosure which follows.

DETAILED DESCRIPTION OF PREFERRED EMBODIMENTS

Example 1

Figure 1:
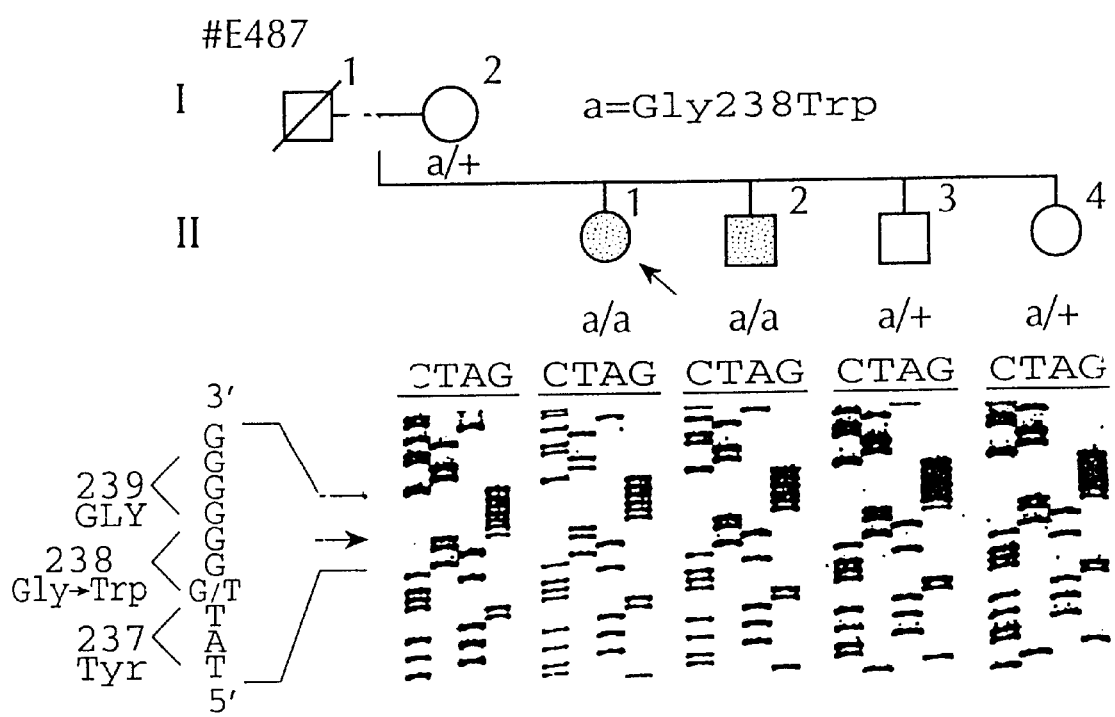
FIG. 1 shows gel analysis of DNA taken from patients, showing mutation at codon 238 of the RDH5 gene.

Given the role of 11-cis retinol dehydrogenase (SEQ ID NO: 1) in vision, it was assumed that patients suffering from hereditary retinal degeneration or malfunction might provide a source of mutated RDH5 genes. Patients with diseases featuring subretinal white or pale yellow spots were chosen for study, because these spots can arise from a lack of vitamin A, and are also found in patients with hereditary retinal degeneration caused by a lack of serum retinol binding protein (Seeliger et al., Invest. Ophthalmol Vis. Sci. 40:3–11 (1999)), or CRALBP (Morimura, et al., Invest. Ophthalmol Vis. Sci. 40:1000–10004 (1999)); Burstedt, et al., Invest. Ophthalmol Vis. Sci. 40:995–1000 (1999)). Twenty nine unrelated patients were evaluated who exhibited retinal degeneration with subretinal spots (retinitis punctata albescens, or albipunctate dystrophy), two patients were evaluated who suffered from night blindness and subretinal spots (fundus albipunctatus), as were 94 normal controls, 71 patients with recessive retinitis pigmentosa, and 73 with dominant retinitis pigmentosa. The latter two groups were used because there were no assurances that the assumption underlying the study, i.e., that mutations would be found in the RDH5 gene of patients who exhibited subretinal spots, would be correct.

The RDH5 gene contains 4 translated exons, Exon 1 is not translated. Single strand confirmation analysis was used to screen the 4 translated exons, as well as flanking intron sequences.

Genomic DNA was analyzed via polymerase chain reaction. Primers were based upon the sequence of RDH5 published by Simon et al., Genomics 36:424–430 (1996), and Gu, et al., (GenBank Acc. No. AF037062), both of which are incorporated by reference and SEQ ID NO: 2. The primer pairs employed were:
5'-GGCCACAGTA AACTGGACM-3'
(nucleotides 2301–2320 of SEQ ID NO:2)(sense)
5'-AGCCGGTGAT GAAGACAAAG-3'
(Nucelotides 2458–2477 of SEQ ID NO:2)(antisense)
which amplify exon 2a of the RDH5 gene;
5'-TTACTCTGGG CAGTGCTGTG-3'
(nucleotides 2399–2418 of SEQ ID NO:2)(sense)
5'-AGGACTCGGA AGCCTCTCTG-3'
(nucleotides 2519–2538 of SEQ ID NO:2)(antisense)
which amplify exon 2b;
5'-TTCTGGCACT GCAGCTGGAC-3'
(nucleotides 2499–2518 of SEQ ID NO:2)(sense)
5'-TTCCTGGTGG TCTACCATAC-3'
(nucleotides 2686–2705 of SEQ ID NO:2)(antisense)
which amplify exon 2c;
5'-CCCCAGCATC CTTTTCATCT-3'
(nucleotides 2848–2867 of SEQ ID NO:2)(sense)
5'-GACGCTGGTG ATGTTGATCA-3'
(nucleotides 3038–3057 of SEQ ID NO:2))(antisense)
which amplify exon 3a;
5'-TGAACACAAT GGGTCCCATC-3'
(nucleotides 2969–2988 of SEQ ID NO:2)(sense)
5'-TGTTAGTCCT GGMCCCAGG-3'
(nucleotides 3151–3170 of SEQ ID NO:2)(antisense)
which amplify exon 3b;
5'-AAGAACCCAG CAACTTCGCT-3'
(nucleotides 4030–4049 of SEQ ID NO:2)(sense)
5'-TTCCCTTCAT GTGCCCCTGT-3'
(nucleotides 5247–5266 of SEQ ID NO:2)(antisense)
which amplify exon 4;
5'-CTGATTGCM CCACCTATGG-3'
(nucleotides 5473–5492 of SEQ ID NO:2)(sense)
5'-AGAGCAGCTT GGCATCCCAA-3'
(nucleotides 5619–5639 of SEQ ID NO:2)(antisense)
which amplify exon 5a; and
5'-TAACCAAGGT GAGCCGATGC-3'
(nucleotides 5549–5568 of SEQ ID NO:2))(sense)
5'-CAATCTCTTG CTGGAAGGCT-3'
(nucleotides 5731–5748 of SEQ ID NO:2)(antisense)
which amplify exon 5b.

Amplification of exon fragments was carried out by isolating DNA from leukocytes of subjects, and then adding 20–100 ng of the DNA to 20 $\mu$l of a solution containing 20 $\mu$M of each pair of the primers described supra, 20 mM Tris-HCl (pH 8. 4), from 0.5 to 1.5 mM $MgCl_2$ (explained infra), 50 mM KCl, 0.02 mM of each of dATP, dTTP, and dGTP, and 0.002 mM of dCTP, 0.6 $\mu$Ci [$\alpha$-$^{32}$P] dCTP (3000 Ci/mmol), 0.1 mg/ml bovine serum albumin, 10% DMSO (except for assays on exons 4 and 5a), and 0.25 units of Taq polymerase.

The amount of $MgCl_2$ varied, depending on the primer pair being used, to obtain optimal amplification. In the assays where exons 2a, 2c and 3b were amplified, 0.5 mM was used. When amplifying exons 2b, 3a, and 5a, 1.0 mM was used, and 1.5 mM was used when amplifying exons 4 and 5b. Samples were heated to 94° C. for 5 minutes to denature the double stranded DNA, and then from 22–30 cycles of amplification were carried out, with a cycle being defined as 30 seconds of denaturing at 94° C., 30 seconds at 50–60° C. for primer annealing, and 30 seconds of extension at 71° C. More specifically, the annealing temperature for exons 2a,3a, and 5a was 58° C., it was 50 ° C. for exons 2c and 3b, and 60° C. for and 5b The final extension involved heating at 71° C. for 5 minutes. In all cases, the pH of the reaction was 8.4.

Amplified DNA was heat denatured, using standard methods, and aliquots of the resulting single stranded fragments were separated through two sets of 6% polyacrylamide gels. One set contained 10% glycerol, and the other did not. Amplification products of the assay for exon 2c were also evaluated by electrophoresis through MDE (mutation detection enhancement) gels. The electrophoresis was carried out for 5–18 hours, at room temperature, and at 8–12 W, before drying and autoradiography. Variant bands (defined as bands migrating at a faster or slower than normal speed through any one of the gels) were evaluated by sequencing the corresponding PCR amplified segments, using standard methods.

The two patients with fundus albipunctatus were found to have missense changes. Specifically, one patient was homozygous for a change in exon 4 at codon 238 (GGG to TGG), (nucleotides 5207–5209 of SEQ ID NO:2) leading to a change in the amino acid encoded by the gene (a change from Gly to Trp), while a second patient was heterozygous for the same change, and for a second change in exon 2 at codon 73 (TCC to TTC)(nucleotides 2589–2591 of SEQ ID NO:2), leading to a change in the amino acid encoded (Ser to Phe). One patient with dominant retinitis pigmentosa exhibited a missense change in exon 2 at codon 33 (ATC to GTC)(nucleotides 2468–2470 of SEQ ID NO:2), leading to an amino acid change (Ile to Val). Silent polymorphisms were also found, at codon 141 (ATC to ATT)(nucleotides 2986–2988 of SEQ ID NO:2) and codon 200 (GTC to GTG)(nucleotides 5093–5095 of SEQ ID NO:2).

Figure 2:
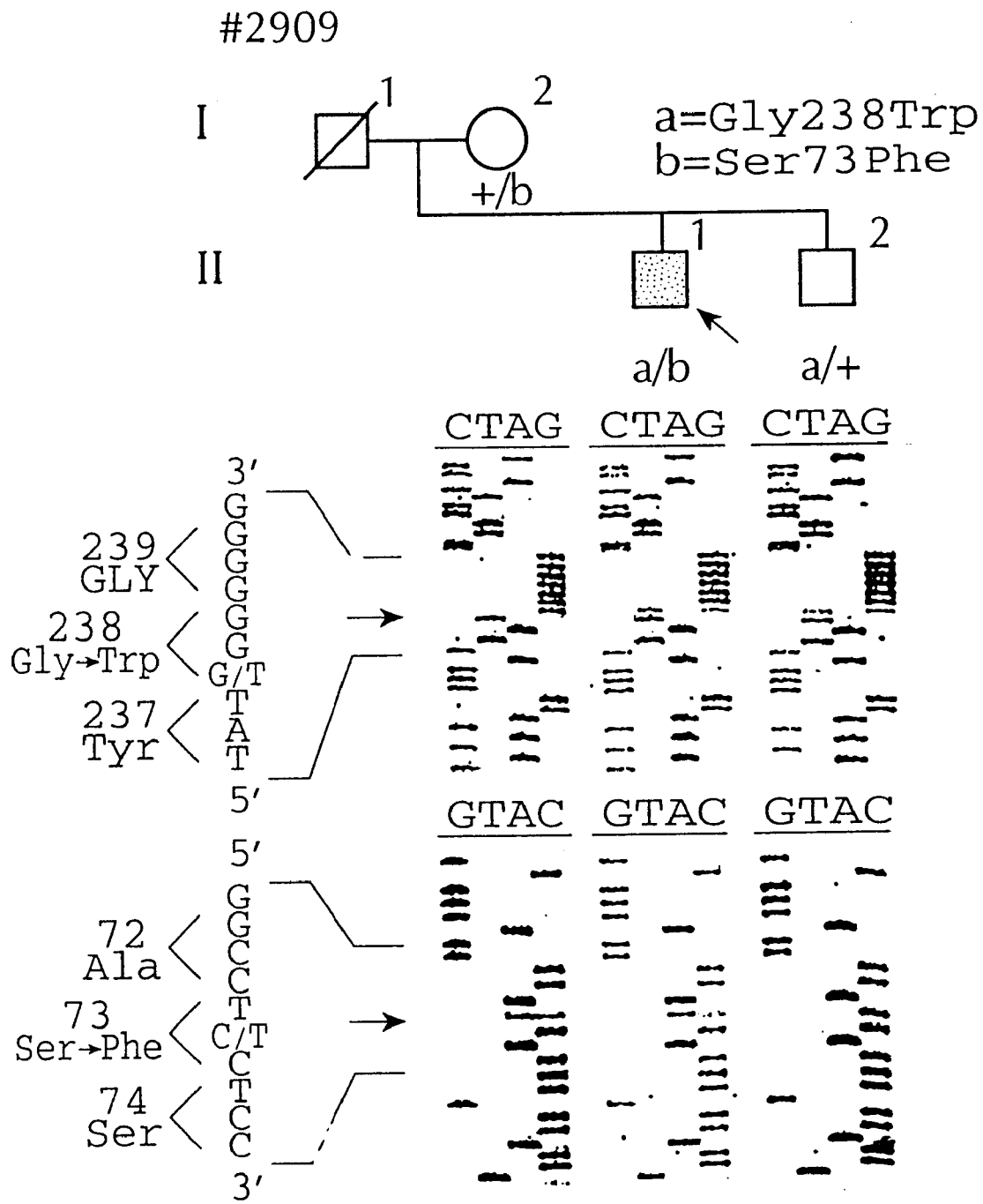
FIG. 2 shows gel analysis of DNA taken from patients, showing mutations at codons 238 and 73

The missense changes at 238 and 73 were studied further via familial analysis. For both subjects, the missense change segregated as would be expected if they caused the disease. For example, a sibling of the patient homozygous for the 238 missense change was also homozygous for the change, and was afflicted with the disease, while the patient's mother and two unafflicted siblings were heterozygous. With respect to the patient who was heterozygous for the missense changes at 238 and 73, there were no affected relatives; however, an unaffected brother was heterozygous for the 238 missense change, and his mother was heterozygous for the 73 missense change. These data are set forth at FIGS. 1 and 2. It can be seen in FIG. 1, for example, afflicted individuals are homozygous for a change at position 238, where "G" has been replaced by "T" in both alleles. In contrast, non afflicted familial individuals are heterozygous for "G" and "T" at this position. The data in FIG. 2 show that individuals can be "compound heterozygotes" in that there are single mutations at both positions 238 and 73. What this indicates is that compound heterozygosity can lead to the condition.

The results show that a homozygous mutation at position 238 is indicative of the condition, i.e., fundus albipunctatus. Heterozygous mutations, i.e., situations where only one allele carried the mutation, did not result in the mutation. On the other hand, the data also evidence compound heterozygosity, in that more than one, heterozygous mutation, results in an abnormal condition.

Example 2

These experiments describe studies to determine the effect of the missense mutations described supra, i.e., Gly238Trp and Ser73Phe on the activity of 11-cis retinol dehydrogenase.

The first set of experiments was designed to generate mutant forms of the enzyme in vitro.

Human cDNA encoding 11-cis retinol dehydrogenase (RDH5)a is known, as per Simon, et al., supra, and allowed U.S. patent application Ser. No. 081258,418, filed Jun. 10, 1994, and PCT W095/34580 published May29, 1997, as SEQ ID NO: 14, all of which are incorporated by reference. See SEQ ID NO: 5 as well. The human cDNA molecule described in these references was subcloned into eukaryotic expression vector pSG5, described by Green, et al., Nudl. Acids Res. 16:369(1988), incorporated by reference. Expression vectors which encoded mutant forms of the enzyme were then generated using single strand mutagenesis, in accordance with Kunkel, et al., Methods Enzymol. 154:367–382 (1987), and Viera, et al., Methods Enzymol. 154:3–11 (1987), both of which are incorporated by reference. The following primers were used to generate the Ser73Phe and Gly238Trp mutants, respectively:

```
5'- CTGCAGCGGG TGGCCTTCTC CCGCCTCCAC    ACC- 3'      (SEQ ID NO:3)

5'- ACACAGGCCC ACTATTGGGG GGCCTTCCTC    ACC- 3'      (SEQ ID NO:4)
```

In SEQ ID NOS: 3 and 4, codons for the missense mutations are underlined.

Following verification that plasmids carried the introduced mutations, these were used to separately transfect COS-1 cells. As controls, expression vectors expressing wild type 11-cis-retinol dehydrogenase (RDH5), or an empty vector were used. All transfections were carried out using the well known DEAE-dextran methodology, as described by Simon, et al., J. Biol. Chem. 270:1107–1112 (1995), incorporated by reference. An expression vector which expressed β-galactosidase (pSVβ gal), which is commercially available, was cotransfected in each experiment. The transfectants were cultured for 48 hours, under standard conditions, after which they were harvested. Microsomes were prepared from these cells, via gentle homogenization and centrifugation at 7000×g for 10 minutes, in order to remove debris, and unbroken cells.

Microsomes were collected from supernatant via centrifugation at 100,000×g for 60 minutes. The microsomes were suspended in PBS, protein concentrations were determined using standard methods, and then aliquots were stored at −80° C., until used. Equal efficiencies of the transfections were verified by measuring β-galactosidase activity using o-nitrophenyl-β-D-galactopyran at 405 nm.

Expression levels of wild type and mutant enzymes were determined via immunoblotting, using pre-existing polyclonal rabbit antiserum, in accordance with the ECL methodology as described by Simon, et al., J. Cell Sci. 112:549–558 (1999).

It was ascertained that both mutants were expressed at levels 8–12 times lower than wild type enzyme.

To monitor the ability of the wild-type and mutant enzymes to catalyze the oxidation of 11-cis retinol to 11-cis retinal, 11-cis retinol, which had been synthesized by reduction of 11-cis retinal with NaBH4 and stored under argon at −80° C., was added to reaction mixtures containing microsomes from the transfected cells. Microsomes containing the wild-type enzyme exhibited the expected ability to catalyze the oxidation of 11-cis retinol to 11-cis retinal in the presence of an excess of the cofactor NAD.

The enzyme reactions, in a total volume of 100 $\mu$p were carried out in 50 mM Tris-HCl buffer pH7.5 containing 5 mM NAD or NADH, 50 M 11-cis retinol, or 11-cis retinal, and microsomes at 37° C. All manipulations of retinoids were performed in dim light. The reactions were stopped by putting the tubes on ice, and the retinoids were immediately extracted with 200 $\mu$l n-hexane. Subsequently, 75 $\mu$l aliquots were analyzed by reverse-phase HPLC using a C18 column. The mobile phase was acetonitrile/water (85/15, v/v), and the column was eluted under isocratic conditions at a flow rate of 1 ml/min. 11-cis retinol and 11-cis retinal eluted at 12.0–12.2 and 14.0–14.3 minutes, respectively. Retinoids were quantified at 320 and 370 nm. To measure the Km and Vmax values of wild type 11-cis retinol dehydrogenase, reactions were carried out as above, using a concentration of 11-cis retinol between 0.5 $\mu$M and 50 M. In these assays, 2 $\mu$g of microsomal protein containing the wild-type enzyme were used in 8-minute incubations. Formed 11-cis retinal was quantified in the HPLC analyses, and the Km and Vmax values were calculated from Lineweaver-Burk plots. The values were compensated for the extraction efficiency (60–70%, as determined experimentally).

The Km and Vmax values for 11-cis retinol in this reaction were determined to be 6.7 M (average of duplicates 5.5 and 7.8), and 8.4 nmol/mg protein/minute (average of duplicates 7.1 and 9. 6)., respectively. These results are consistent with a report by Wang, et al., Biochem. J. 338:23 (1999). As expected, the wild-type enzyme was also able to catalyze the reverse reaction, i.e., the reduction of 11-cis retinal to 11-cis retinol, in the presence of an excess of NADH.

The relative activities of the wild type and mutant enzymes were then determined. To do this, microsomes containing a mutant enzyme (20 $\mu$g), or wild type enzyme(2 $\mu$g) together with 18 $\mu$g of microsomal protein from mock-transfected cells, to standardize the experimental conditions, or no enzyme were combined with 50 mM Tris-HCl buffer (pH 7.5), containing 5 mM of NAD, and 50 $\mu$M 11-cis-retinol (forward, oxidation reaction) or 5 mM NADH and 50 $\mu$M 11-cis-retinal (reverse, reduction reaction) in a total volume of 100 $\mu$l. 50 $\mu$M 11-cis retinol is approximately a seven-fold higher substrate concentration than the estimated Km value for the wild-type enzyme. The mixtures were incubated for 10 minutes at 37° C., after which the reactions were stopped by putting the mixtures on ice. Retinoids were extracted immediately with 200 $\mu$l of n-hexane. Subsequently, 75 $\mu$l aliquots were analyzed via reversed phase HPLC using a $C_{18}$ column. The mobile phase was acetonitrile/water (85:15 v/v), and the column was eluted under isocratic conditions at a flow rate of 1 ml/min. The 11-cis-retinol eluted at 12.0–12.2 minutes, and 11-cis-retinal at 14.0–14.3 minutes. Retinoids were quantified at 320 (retinol) and 370 (retinal) nm. Relative activities of wild-type and mutant enzymes were calculated as the ratio of formed 11-cis retinal by transfected versus mock-transfected microsomes. The results were normalized for the total extracted retinoid content from each reaction.

The wild type enzyme exhibited the expected ability to catalyze the oxidation of 11-cis-retinol to 11-cis-retinal in the presence of an excess of NAD. Similarly, it catalyzed the reverse reaction, i.e., reduction of 11-cis-retinal to 11-cis-retinol, in the presence of excess NADH.

Both mutants exhibited dramatic reductions in their ability to catalyze the relevant reactions, even though they were used at 10 fold higher concentrations in view of their lower expression levels. The Gly238Trp mutant showed no activity above background level, while the Ser73Phe mutant showed residual activity. Similar results were obtained when catalyzing the reverse reaction.

The Gly238Trp mutant was tested further, to determine if it had any activity, by incubating for 20 and 40 minute periods before extracting retinoids. Wild type and Ser73Phe mutant were used as controls. The Gly238Trp mutant showed 2.2±0.14 fold activity above background activity (using mock transformants), as compared to 42.9+4.5 fold (wild type), and 9.1±1 fold (Ser273Phe), after 40 minutes. This indicates that the Ser 73Phe mutant has approximately 5 fold less activity, and the Gly238Trp mutant approximately 19 fold less activity than wild type enzyme.

The foregoing examples describe the invention, which relates to mutations in the nucleic acid molecule which encodes 11-cis retinol dehydrogenase, as well as the resulting mutated protein. Specifically, mutations at the codon which encodes amino acid 238 and/or the codon which encodes amino acid 73 are a feature of the invention. In particular, with respect to codon 238 Trp, rather than Gly, is encoded, and with respect to amino acid 73Phe, rather than Ser, is encoded. Also a feature of the invention are molecules where the mutation is at position 33, especially those where Val, rather than lie is encoded. In addition to the specific mutations described supra, it will be understood by the skilled artisan that, in view of codon degeneracy, more than one type of mutation may result in the specific changes.

As was explained, supra, the mutated forms of the encoding molecules and the proteins are involved in ocular disorders. Hence, a further feature of this invention is the determination of the possible presence of an ocular disorder, via determining presence of a mutated form of either the nucleic acid molecule, the protein, or both. Such methods include, e.g., hybridization assays such as the polymerase chain reaction, antibody assays involving antibodies specific for an epitope defined by the mutation, and so forth. One specific type of disorder which may be determined via these methodologies is fundus albipunctatus.

Fundus albipunctatus is a form of night blindness wherein patients who suffer from rod photoreceptor malfunction recover after prolonged exposure to darkness. This condition is characterized further by delays in recovery of both rod and cone function after exposure to light; however, fundus albipunctatus is characterized as a form of night blindness, because cone recovery from exposure to light is generally not sufficiently impaired to be subjectively important.

The experiments set forth supra show that the abnormally slow rates of regeneration of code and rod photopigment found in fundus albipunctatus result from slower than normal rates of production of 11-cis retinal, due to reduced 11-cis retinol dehydrogenase activity. Further, decreased, steady state levels of mutant enzymes were seen, suggesting folding or stability problems. Indeed, these two phenomena point to a net capacity of the enzyme to generate 11-cis retinal at one order of magnitude lower than normal. These observations suggest a further application of the invention, which is the treatment of conditions characterized by mutations in the gene encoding 11-cis retinal dehydrogenase, or mutated forms of the protein, by administration of an amount of normal, or, "wild type" 11-cis retinal dehydrogenase sufficient to alleviate the disorder. Similarly, since the enzyme is involved in the production of 11-cis retinal, the therapy can also take the form of administration of 11-cis-retinal, in any of the standard forms of ocular administration. Similarly, principles of gene therapy, such as homologous recombination, can be employed to correct the mutation, upon its detection.

As the mutated forms of the enzyme are useful in the ways discussed supra, it is desirable to have a ready source of the materials. Hence, another feature of this invention is the recombinant production of the enzyme, via the use of transformed or transected cells, where the resulting recombinant cells produce the mutant enzyme, as well as multiple copies of the desired nucleic acid molecule.

Mutations in the nucleic acid molecule, in addition to those described above, i.e., at codons for amino acids 238, or 73, or 33, which result in inactive or less active forms of the enzyme, are also a part of this invention. These mutations can include other missense changes, as well as deletions, insertions, frame shift mutations, mutations affecting intron splice donor or acceptor sites, mutations in the promotor region, and so forth Identification of such mutations via, e.g., PCR, or other forms of assays, are indicative of possible presence of an optical disorder.

Other features of the invention will be clear to the skilled artisan, and are not set forth herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule which encodes a protein, the amino acid sequence of which is set forth in SEQ ID NO: 1, with the proviso that (i) amino acid 238 is not Gly, or (ii) amino acid 73 is not Ser, or (iii) amino acid 33 is not Ile.

2. An isolated nucleic acid molecule which encodes the protein of claim 1, wherein amino acid 238 is Trp rather than Gly.

3. An isolated nucleic acid molecule which encodes the protein of claim 1, wherein amino acid 73 is Phe rather than Ser.

4. An isolated nucleic acid molecule which encodes the protein of claim 1, wherein amino acid 33 is Val rather than Ile.

5. An expression vector comprising the isolated nucleic acid molecule of claim 1, operably linked to a promoter.

6. A recombinant host cell comprising the isolated nucleic acid molecule of claim 1.

7. A recombinant host cell comprising the expression vector of claim 5.

* * * * *

UNITED STATES PATENT AND TRADEMARK OFFICE
CERTIFICATE OF CORRECTION

PATENT NO. : 6,358,728 B1 Page 1 of 1
DATED : March 19, 2002
INVENTOR(S) : Simon et al.

It is certified that error appears in the above-identified patent and that said Letters Patent is hereby corrected as shown below:

<u>Column 1,</u>
Prior to line 10 add:
-- STATEMENT REGARDING FEDERALLY
SPONSORED RESEARCH OR DEVELOPMENT The invention described in this patent application was supported in part by National Institute of Health grants EY0683 and EY00169. --

Signed and Sealed this

Thirtieth Day of July, 2002

*Attest:*

*Attesting Officer*

JAMES E. ROGAN
*Director of the United States Patent and Trademark Office*

```
                           SEQUENCE LISTING

<160> NUMBER OF SEQ ID NOS: 5

<210> SEQ ID NO 1
<211> LENGTH: 318
<212> TYPE: PRT
<213> ORGANISM: Homo sapiens

<400> SEQUENCE: 1

Met Trp Leu Pro Leu Leu Leu Gly Ala Leu Leu Trp Ala Val Leu Trp
1               5                   10                  15

Leu Leu Arg Asp Arg Gln Ser Leu Pro Ala Ser Asn Ala Phe Val Phe
            20                  25                  30

Ile Thr Gly Cys Asp Ser Gly Phe Gly Arg Leu Leu Ala Leu Gln Leu
        35                  40                  45

Asp Gln Arg Gly Phe Arg Val Leu Ala Ser Cys Leu Thr Pro Ser Gly
    50                  55                  60

Ala Glu Asp Leu Gln Arg Val Ala Ser Ser Arg Leu His Thr Thr Leu
65                  70                  75                  80

Leu Asp Ile Thr Asp Pro Gln Ser Val Gln Gln Ala Ala Lys Trp Val
                85                  90                  95

Glu Met His Val Lys Glu Ala Gly Leu Phe Gly Leu Val Asn Asn Ala
            100                 105                 110

Gly Val Ala Gly Ile Ile Gly Pro Thr Pro Trp Leu Thr Arg Asp Asp
        115                 120                 125

Phe Gln Arg Val Leu Asn Val Asn Thr Met Gly Pro Ile Gly Val Thr
    130                 135                 140

Leu Ala Leu Leu Pro Leu Leu Gln Gln Ala Arg Gly Arg Val Ile Asn
145                 150                 155                 160

Ile Thr Ser Val Leu Gly Arg Leu Ala Ala Asn Gly Gly Gly Tyr Cys
                165                 170                 175

Val Ser Lys Phe Gly Leu Glu Ala Phe Ser Asp Ser Leu Arg Arg Asp
            180                 185                 190

Val Ala His Phe Gly Ile Arg Val Ser Ile Val Glu Pro Gly Phe Phe
        195                 200                 205
```

Arg Thr Pro Val Thr Asn Leu Glu Ser Leu Glu Lys Thr Leu Gln Ala
        210                 215                 220

Cys Trp Ala Arg Leu Pro Pro Ala Thr Gln Ala His Tyr Gly Gly Ala
225                 230                 235                 240

Phe Leu Thr Lys Tyr Leu Lys Met Gln Gln Arg Ile Met Asn Leu Ile
                245                 250                 255

Cys Asp Pro Asp Leu Thr Lys Val Ser Arg Cys Leu Glu His Ala Leu
            260                 265                 270

Thr Ala Arg His Pro Arg Thr Arg Tyr Ser Pro Gly Trp Asp Ala Lys
        275                 280                 285

Leu Leu Trp Leu Pro Ala Ser Tyr Leu Pro Ala Ser Leu Val Asp Ala
        290                 295                 300

Val Leu Thr Trp Val Leu Pro Lys Pro Ala Gln Ala Val Tyr
305                 310                 315

<210> SEQ ID NO 2
<211> LENGTH: 6330
<212> TYPE: DNA
<213> ORGANISM: Homo sapiens
<220> FEATURE:
<221> NAME/KEY: unsure
<222> LOCATION: 5357, 5448
<223> OTHER INFORMATION: nucleotide not determined

<400> SEQUENCE: 2

| | | | | | |
|---|---|---|---|---|---|
| ccaggttttc | cctcccttcc | cccactcagc | tgcaggaact | ccttttttggg | gtttggatct | 60 |
| ggtattttc | tattcagctc | cgagcttggc | tctcctgggg | aatcctggga | gtgaaaggaa | 120 |
| ggagctgggt | ttatttgcat | gtactggtag | tcatttgcat | cacatccaaa | atggccaaa | 180 |
| attataaccc | ctgattcttg | gctgaactgg | gactgctgca | atggaatatt | attcccggaa | 240 |
| accaccccca | actagctgga | gctaatctcc | tccctcctcc | aacccccat | tttggcccag | 300 |
| gcctacataa | accaaaaaaa | gctggaccat | aaggtgaaaa | ccctacaggt | ccaggctgcc | 360 |
| caatttgcca | agcaaacagg | ccattggatc | gaaatggtga | aaaacttcaa | ccaggcactc | 420 |
| aaggtgggcc | atactcccta | cctcaccacc | ccaatcctgg | gcccccattg | gctgcctcca | 480 |
| gtcaggttac | ctcaggttta | ggttaaggag | gaagtagggt | ggtcccagaa | accccatcta | 540 |
| tagccccagt | gtcagaaaag | gttgagaaag | aaagaaaagc | agttggtggg | tccaagttaa | 600 |
| agccttttcc | aggagatgaa | taaaacttat | tccccaatgg | aagccatagt | ctacccattc | 660 |
| tgattcctgg | gtcccaactc | ctctccccct | ttccaggaaa | ttggggatgt | ggagaatggg | 720 |
| cttggagcat | tgagctggaa | atgcgcacca | ttgccaatgc | aatggaatat | gtttacaaag | 780 |
| ggcagctgca | gtttgcccct | tcctagcccc | tgttccctcc | cccaaccta | tccctcctac | 840 |
| ctcacccgca | gggggaagga | gggaggctga | caagccttga | ataaaaaaca | agcctccgtt | 900 |
| tttttgtggt | gtgtttcaga | gaggtaatag | ctccagtgtc | ggggtggga | gtggaaggtt | 960 |
| caaaggtggt | ttccctgagg | gacaggtacc | ttttggggag | agggtggaaa | tagcttcctt | 1020 |
| ttactatccc | aaatttttttt | tcctccatgg | cccttgtgca | ggtgtttgtt | aggcaagcag | 1080 |
| agggtgggag | ttcccatccc | tcctgagaga | aggtcctagt | agccctgccc | caagcttcct | 1140 |
| aattcaggaa | ttgttttccta | cagaagagaa | acaaggcaag | tacacctggt | ccccagctct | 1200 |
| ggctttctgc | ctctccacgt | gctcatggcc | tctcccagg | ctaactctaa | gcagtgtcat | 1260 |
| gagtctgagc | caggtgggag | attaattcct | gggggcactt | cagggctgag | aagggggagg | 1320 |
| aatgacaggt | ccagtaaccg | ttaccaacag | agcagtgcag | ctgccatcct | tgacagctcc | 1380 |

```
ctcctccttg gagaccatga catagatggt caggaaccca ggctgagaaa gacagccaag    1440
gggtgggggg agcctaggca aatctggcct ctgccaagtc ctggcttcag ccaggcaagc    1500
tccagcctcc ctggctcctc ctcctcctca gtcctatccc caccctgtca cacatacact    1560
taatacgcct ggcatccaag tccacccact ccggactttg ccttagcag tagttagtgt    1620 gggaggctgg gaagactggg agcagtctct taaacaaaag caaagaata agcttcgggc    1680 gctgtagtac ctgccagctt tcgccacagg aggtaagtgg atctgggagc tgggggaact    1740
gagaagacta gccagatatt acatgtattg ccaactcaaa actttcagct tttaacatgc    1800
ttcctcacac attatcccct ttgatcctcc acaactctga ggtggacctg gtgggtctta    1860
gccccacttg gtagatgaga aaataggttg agagagacag tgagatgctc agtatcacac    1920
agcaaacctc ttggccctat acatcattcc aaacacaaga cccaggttgc atatagaagg    1980
ttcagtgtcc ctggtttaga aggagaggtg gtgtgaggca agcaagaaga tgcctctgct    2040
gcactccagc ctgggcgaca gagtgagact ccatctcaaa aaaaaaaaa aacgatgcct    2100 ctgctcccata cagcaggtct gtacacagga tctggctcat gtggttttag ttaagttagc    2160
cacaaataca gggtctgccc acatctttgc tttgaacaga tgagccatgg ttggccaatt    2220
atctgccaac cagataattt ctcaatatgc tcacaccaga tgcttccagc tagggagggt    2280
attaggggaa agggcttgag ggccacagta aactggacaa gttttttctgc ccagcctagg    2340 ctgccacctg taggtcactt gggctccagc tatgtggctg cctcttctgc tgggtgcctt    2400
actctgggca gtgctgtggt tgctcaggga ccggcagagc ctgcccgcca gcaatgcctt    2460
tgtcttcatc accggctgtg actcaggctt gggcgccctt ctggcactgc agctggacca    2520
gagaggcttc cgagtcctgg ccagctgcct gaccccctcc ggggccgagg acctgcagcg    2580
ggtggcctcc tcccgcctcc acaccaccct gttggatatc actgatcccc agagcgtcca    2640
gcaggcagcc aagtgggtgg agatgcacgt taaggaagca ggtaagtatg gtagaccacc    2700
aggaatatgg tgtgggtgt cctgatcccc acagtcaccc caggagtcac ctgcaagggc    2760
tgtggtaagc taaagggaca atttgaggag aagcagtttt cagatgctcc caggaagaag    2820
agggagctgt gggagtgcct cacctacccc cagcatcctt ttcatctccc cacagggctt    2880
tttggtctgg tgaataatgc tggtgtggct ggtatcatcg gacccacacc atggctgacc    2940
cgggacgatt tccagcgggt gctgaatgtg aacacaatgg gtcccatcgg ggtcacccttt   3000 gccctgctgc ctctgctgca gcaagcccgg ggccgggtga tcaacatcac cagcgtcctg    3060
ggtcgcctgg cagccaatgg tgggggctac tgtgtctcca aatttggcct ggaggccttc    3120
tctgacagcc tgaggtgagg ggtacagggc tctgggttcc aggactaaca gcagcccact    3180
caacaaacgt gggccagcag aggtggttaa aatacagcac attggaatag ttaaaaagag    3240
acagtttagg gctaaacttc atgggttcaa tgaagtctac ccttatgtaa gctttgtgac    3300
cataagtaga ttacttctct ttacccattt ttaacgtgtt tgttttttgt tttttgagat    3360
ggagtcttgc tctgtcgcca ggctggagtg cagtggcgcg atcttggctc accacaattt    3420 ccaccccgg ggttcaagcg attctcctgc ctcagcctcc cgagtagctg ggactacagg    3480
catgcgccac catgcctggc taattttttgt attttttagta gagacagggt ttcactatgt    3540
tggccaggtt ggtctcaaac tcctgacctc gtgatccgcc cacctcagcc tcccaaagtg    3600
ctgggattac aggtgtgagc caccacgccc ggccttgcct ctcgtcttta aacaataagg    3660
ttcaaagttc cgtgggagca caaaggagac atgatgagga caacgggagt tagggcctga    3720
```

```
gttttttttgg ttttttttttt ttaagcgttt tgctcttgtt gcctaggctg gagtgcaatg    3780
gcgagatctc agctcacagc aacccctgcc tctcaggttc atgtgattct cctgcctcag    3840
cctcccgatt agctgggctt acaggcacgt gccaccactc ccagctaaat ttttaggtag    3900
agatggagtt tataccatgt ggccagggtg ggtttgaatt cctgacctca cctgatccac    3960
cggaccggcc ttcccaaagt gctgggatta caggcatgag ccaccacaca cggcccaagg    4020
cctgagttct tagcaggagt ataaggcgcc taagcttagt ctaccttcta aggaagcctg    4080
cgtttgtcac catcactcag caaataaccg aattgtctc ctgtctctca gccttaattt     4140
ttcaggcagc atcatgggac atactttt agttttgaga caaggccttg ctctcaccca      4200
gggtggagtg cagtggtgca gtcacggccc actgaacttc aaactcctag gctcaagcag    4260
ctcaagcgat atccgcctca gcctcctgag tagctgagac acaggcgcg tgccagcatg     4320 cctggctagt atttttttac agatgggtc ttgctgtggt gaccagactt gtctccaact     4380
cccggcctca agcgatgctt ccgcctgggc ctcccaaagt gttgggatta taggtgtgag    4440
ccactgcata ctgaacaca tactttatac ttgaatttt ttttatcccc ttccttcgtg      4500
ctcctaacct atacttggat ttctacatct gtgccagggc agtgggatgt atccccactt    4560
tccccatcag cttaccctcc agcaaatacg agactatacc cttcaatatc cagcactcag    4620
ggctcaacca tgtgttttgg gagcaaggga atggggttcc tctaggtcag gaatcggcaa    4680
actcagtact caagccagat ttggccagct gcctacaagc tgataatggt ttttttatt     4740 tttaaatggt tacattgtaa actgttatat aagtacctga taatatcatt aattttgttt    4800
cttggcctgc catgcttaaa atattaactc tctggcccct taagaaaaaa acgtgctgac    4860
ccctgctcta gatcaaagaa acaaacctc aaaaatactt tcctccctct accccacttg     4920
acccttgtcc cggggcagta ggcatctccg tcaaaactct tgtccctggt ctgtggtaac    4980
tttctcagct ccccaaccca tgtccctcaa agtcccctcc ctatagggca agaacccagc    5040
aacttcgctc tgccccgact ctaggcggga tgtagctcat tttgggatac gagtctccat    5100
cgtggagcct ggcttcttcc gaaccctgt gaccaacctg gagagtctgg agaaaaccct    5160
gcaggcctgc tgggcacggc tgcctcctgc cacacaggcc cactatgggg gggccttcct   5220
caccaagtgt gagtagccag gcccacacag gggcacatga agggaaacaa gtaccagaaa    5280
ggccagtcct gcataagcct gctaggaggt gggtggggca cccagggcag ggttgagggt    5340
gaacaggatg ttacaanagt gcccaggcca tgtggaacct gcccactccc cacactgagg    5400 agggggactga gggtgacaag cccagggccc caaaaaacag tacctaanat gggctggagt   5460
gaggaaggga aactgattgc aaccaccat ggggctgcag acctgaaaat gcaacagcgc    5520
atcatgaacc tgatctgtga cccggaccta accaaggtga ccgatgcct ggagcatgcc   5580 ctgactgctc gacacccccg aacccgctac agcccaggtt gggatgccaa gctgctctgg    5640
ctgcctgcct cctacctgcc agccagcctg gtggatgctg tgctcacctg ggtccttccc    5700
aagcctgccc aagcagtcta ctgaatccag ccttccagca agagattgtt tttcaaggac    5760
aaggactttg atttatttct gcccccaccc tggtactgcc tggtgcctgc cacaaaataa    5820
gcactaacaa aagtgtattg tttaaaaat aaaagaagg tgggcagaaa tgtgcccagt    5880
ggaaggctga ccccatttaa gtgccaacta ctccaaaccg acatgctcac ggtctctggc    5940
ctgttcagtc cctgcaaaac agctagcacc cacagtgggg cgccaggaa ctgcctcaca    6000 tctacagctg cacgtcgggg agtggccatc aaagggcact ttaatacatt tcccttattt    6060
tctgaagggg agtaaggttg caattcagtg tctgtactgg gaatggtctt catatttctt    6120
```

```
gggggagaag agcaggtgat gagggttctg ggccaggctg ggtggcttcc atggaagaaa      6180
aggcaatatt cacataaatt ctcctgctaa ggacactgac cacacaggtg tgcaaggcaa      6240
cttatcatac ttcgaaagga gctggatccc ttgaggattg ccaggaagg gaggtgctgg       6300 gcccttagcg gtgcacagaa ggccaggaag                                       6330

<210> SEQ ID NO 3
<211> LENGTH: 33
<212> TYPE: DNA
<213> ORGANISM: Homo sapiens

<400> SEQUENCE: 3
ctgcagcggg tggccttctc ccgcctccac acc                                   33

<210> SEQ ID NO 4
<211> LENGTH: 33
<212> TYPE: DNA
<213> ORGANISM: Homo sapiens

<400> SEQUENCE: 4
acacaggccc actattgggg ggccttcctc acc                                   33

<210> SEQ ID NO 5
<211> LENGTH: 1128
<212> TYPE: DNA
<213> ORGANISM: Homo sapiens

<400> SEQUENCE: 5
taagcttcgg gcgctgtagt acctgccagc tttcgccaca ggaggctgcc acctgtaggt      60
cacttgggct ccagctatgt ggctgcctct tctgctgggt gccttactct gggcagtgct     120
gtggttgctc agggaccggc agagcctgcc cgccagcaat gcctttgtct tcatcaccgg     180
ctgtgactca ggctttgggc gccttctggc actgcagctg gaccagagag gcttccgagt     240
cctggccagc tgcctgaccc cctccgggc cgaggacctg cagcgggtgg cctcctcccg     300
cctccacacc accctgttgg atatcactga tcccagagc gtccagcagg cagccaagtg     360
ggtggagatg cacgttaagg aagcagggct ttttggtctg gtgaataatg ctggtgtggc     420
tggtatcatc ggacccacac catggctgac ccgggacgat ttccagcggg tgctgaatgt     480
gaacacaatg ggtcccatcg gggtcaccct tgccctgctg cctctgctgc agcaagcccg     540
gggccgggtg atcaacatca ccagcgtcct gggtcgcctg gcagccaatg gtggggcta    600 ctgtgtctcc aaatttggcc tggaggcctt ctctgacagc ctgaggcggg atgtagctca     660
ttttgggata cgagtctcca tcgtggagcc tggcttcttc cgaacccctg tgaccaacct     720
ggagagtctg gagaaaaccc tgcaggcctg ctgggcacgg ctgcctcctg ccacacaggc     780
ccactatggg ggggccttcc tcaccaagta cctgaaaatg caacagcgca tcatgaacct     840
gatctgtgac ccggacctaa ccaaggtgag ccgatgcctg gagcatgccc tgactgctcg     900 acaccccga acccgctaca gcccaggttg ggatgccaag ctgctctggc tgcctgcctc     960
ctacctgcca gccagcctgg tggatgctgt gctcacctgg gtccttccca gcctgcccca    1020
agcagtctac tgaatccagc cttccagcaa gagattgttt ttcaaggaca aggactttga    1080
tttatttctg ccccccaccct ggtactgcct ggtgcctgcc acaaaata              1128
```